United States Patent [19]
Gaster et al.

[11] Patent Number: 5,705,509
[45] Date of Patent: Jan. 6, 1998

[54] TRICYCLIC HETEROCYCLIC COMPOUNDS AS 5-HT$_4$ RECEPTOR ANTAGONISTS

[75] Inventors: Laramie Mary Gaster, Bishop's Stortford; Paul Adrian Wyman, Epping, both of England

[73] Assignee: SmithKline Beecham plc, Brentford, United Kingdom

[21] Appl. No.: 495,538

[22] PCT Filed: Jan. 28, 1994

[86] PCT No.: PCT/GB94/00172

§ 371 Date: Jul. 28, 1995

§ 102(e) Date: Jul. 28, 1995

[87] PCT Pub. No.: WO94/17071

PCT Pub. Date: Aug. 4, 1994

[30] Foreign Application Priority Data

Jan. 28, 1993 [GB] United Kingdom ............... 9301660

[51] Int. Cl.$^6$ .................. A61K 31/445; C07D 401/14
[52] U.S. Cl. .................. 514/322; 514/213; 514/319; 514/320; 514/321; 514/323; 514/324; 514/325; 514/366; 514/375; 514/394; 514/411; 514/422; 514/408; 514/183; 540/450; 540/480; 540/602; 540/603; 540/609; 540/610; 546/197; 546/198; 546/199; 546/200; 546/202; 548/150; 548/151; 548/217; 548/218; 548/302.1; 548/430; 548/429; 548/427; 548/528; 548/525; 548/526; 548/527
[58] Field of Search .................. 514/366, 375, 514/394, 411, 321, 322, 212, 183, 213, 319–325, 422, 408; 540/480, 596, 450, 602, 603, 609, 610; 546/197–199, 200, 202, 196; 548/150, 151, 217, 218, 302.1, 430, 433, 427, 429, 525–528

[56] References Cited

U.S. PATENT DOCUMENTS

| | | | |
|---|---|---|---|
| 3,732,245 | 5/1973 | Batcho et al. | 548/508 |
| 4,186,135 | 1/1980 | Thominet et al. | 548/526 |
| 4,499,099 | 2/1985 | Watts | 514/299 |
| 4,772,459 | 9/1988 | Sun et al. | 424/649 |
| 4,797,406 | 1/1989 | Richardson et al. | 514/299 |
| 5,185,335 | 2/1993 | Van Daele et al. | 514/243 |
| 5,196,547 | 3/1993 | Becker et al. | 548/453 |
| 5,374,637 | 12/1994 | Van Daele et al. | 514/320 |

FOREIGN PATENT DOCUMENTS

| | | |
|---|---|---|
| 0 501 322 A1 | 9/1992 | European Pat. Off. |
| WO91/13872 | 9/1991 | WIPO |
| WO 9116045 | 10/1991 | WIPO |
| WO93/05038 | 3/1993 | WIPO |

*Primary Examiner*—C. Warren Ivy
*Assistant Examiner*—Garth M. Dahlen
*Attorney, Agent, or Firm*—Charles M. Kinzig; Edward T. Lentz

[57] ABSTRACT

Compounds of formula (I) or a pharmaceutically acceptable salt thereof, wherein $X_1$—$(CH_2)_x$—$X_2$ and the aromatic carbon atoms to which they are attached form 5–7 membered ring wherein $X_1$ is O or S; $X_2$ is O, S, $NR_5$ or $NR_6CO$ wherein $R_5$ is hydrogen or $C_{1-6}$ alkyl; or one of $X_1$ and $X_2$ is O, S or $CH_2$ and the other is $CH_2$; x is 1, 2 or 3; $R_1$ and $R_2$ together are Q—$CH_2$—$CH_2$, Q—CH=CH, or Q—CH=N where Q is linked either to the $R_1$ or the $R_2$ substitution position and Q is O, S or $NR_t$ wherein $R_t$ is hydrogen or $C_{1-6}$ alkyl; $R_3$ is hydrogen halo, $C_{1-6}$ alkyl, $C_{1-6}$ alkoxy or amino; $R_4^1$ and $R_4^2$ are independently hydrogen or $C_{1-6}$ alkyl; Y is O or NH; Z is of sub-formula (a), (b) or (c) and their use as pharmaceuticals in the treatment of gastrointestinal disorders, cardiovascular disorders and CNS disorders.

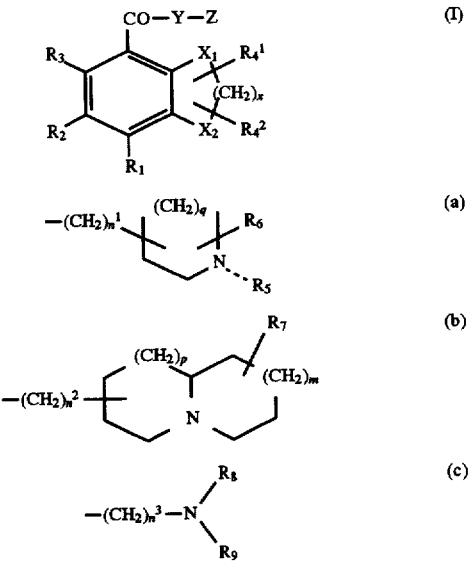

14 Claims, No Drawings

TRICYCLIC HETEROCYCLIC COMPOUNDS AS 5-HT$_4$ RECEPTOR ANTAGONISTS

This application is a 371 of PCT/GB94/00172, Jan. 28, 1994.

This invention relates to novel compounds having pharmacological activity, to a process for their preparation and to their use as pharmaceuticals.

European Journal of Pharmacology 146 (1988), 187–188, and Naunyn-Schmiedeberg's Arch. Pharmacol. (1989) 340:403–410, describe a non classical 5-hydroxytryptamine receptor, now designated the 5-HT$_4$ receptor, and that ICS 205-930, which is also a 5-HT$_3$ receptor antagonist, acts as an antagonist at this receptor.

WO 91/16045 (SmithKline and French Laboratories Limited) describes the use of cardiac 5-HT$_4$ receptor antagonists in the treatment of atrial arrhythmias and stroke.

EP-A-501322 (Glaxo Group Limited), WO 93/02677, WO 93/03725, WO 93/05038, WO 93/05040, WO 93/18036, and PCT/EP93/03054 (SmithKline Beecham plc) describe compounds having 5-HT$_4$ receptor antagonist activity.

It has now been discovered that certain novel compounds also have 5-HT$_4$ receptor antagonist properties.

EP-A-234872 (Adria), U.S. Pat. No. 4,859,683 (Rorer) and EP-A-307 172 (Lilly) describe 5-HT$_3$ receptor antagonists derived from a benzoic acid nucleus, 2,3-disubstituted by alkyleneoxy.

A class of novel, structurally distinct compounds has now been discovered, which compounds are fused tricyclic derivatives incorporating and linking through a core which is a phenyl ring. These compounds have 5-HT$_4$ receptor antagonist activity.

Accordingly, the present invention provides a compound of formula (I), or a pharmaceutically acceptable salt thereof:

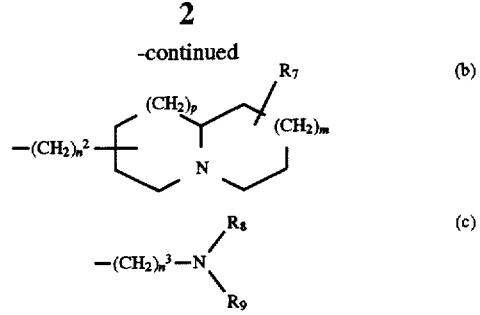

(I)

wherein
in which $X_1$—$(CH_2)_x$—$X_2$ and the aromatic carbon atoms to which they are attached form a 5–7 membered ring
wherein
$X_1$ is O or S; $X_2$ is O, S, $NR_r$ or $NR_rCO$ wherein $R_r$ is hydrogen or $C_{1-6}$ alkyl; or
one of $X_1$ and $X_2$ is O, S or $CH_2$ and the other is $CH_2$;
x is 1, 2 or 3;
$R_1$ and $R_2$ together are Q—$CH_2$—$CH_2$, Q—CH=CH, or Q—CH=N where Q is linked either to the $R_1$ or the $R_2$ substitution position and Q is O, S or $NR_r$ wherein $R_r$ is hydrogen or $C_{1-6}$ alkyl;
$R_3$ is hydrogen, halo, $C_{1-6}$ alkyl, $C_{1-6}$ alkoxy or amino;
$R_4^1$ and $R_4^2$ are independently hydrogen or $C_{1-6}$ alkyl;
Y is O or NH;
Z is of sub-formula (a), (b) or (c):

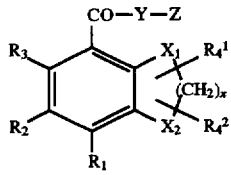

(a)

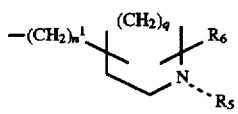

(b)

(c)

wherein
$n^1$ is 1, 2, 3 or 4; $n^2$ is 0, 1, 2, 3 or 4; $n^3$ is 2, 3, 4 or 5;
q is 0, 1, 2 or 3; p is 0, 1 or 2; m is 0, 1 or 2;
$R_5$ is hydrogen, $C_{1-12}$ alkyl, aralkyl or $R_5$ is $(CH_2)_z$—$R_{10}$ wherein z is 2 or 3 and $R_{10}$ is selected from cyano, hydroxyl, $C_{1-6}$ alkoxy, phenoxy, $C(O)C_{1-6}$ alkyl, $COC_6H_5$, —$CONR_{11}R_{12}$, $NR_{11}COR_{12}$, $SO_2NR_{11}R_{12}$ or $NR_{11}SO_2R_{12}$ wherein $R_{11}$ and $R_{12}$ are hydrogen or $C_{1-6}$ alkyl; or $R_5$ is straight or branched chain alkylene of chain length 1–6 carbon atoms terminally substituted by aryl, 3 to 8 membered cycloalkyl, 3 to 8 membered heterocyclyl, 5 or 6 membered monocyclic heteroaryl or 9 or 10 membered fused bicyclic heteroaryl linked through carbon, $C_{2-7}$ alkoxycarbonyl, or secondary or tertiary hydroxy substituted $C_{1-6}$ alkyl; and
$R_6$, $R_7$ and $R_8$ are independently hydrogen or $C_{1-6}$ alkyl; and
$R_9$ is hydrogen or $C_{1-10}$ alkyl;
or a compound of formula (I) wherein the CO—Y linkage is replaced by a heterocyclic bioisostere;
having 5-HT$_4$ receptor antagonist activity.

Examples of alkyl or alkyl containing groups include $C_1$, $C_2$, $C_3$, $C_4$, $C_5$, $C_6$, $C_7$, $C_8$, $C_9$, $C_{10}$, $C_{11}$ or $C_{12}$ branched, straight chained or cyclic alkyl, as appropriate. $C_{1-4}$ alkyl groups include methyl, ethyl, n- and iso-propyl, n-, iso-, sec- and tert-butyl. Cyclic alkyl includes cyclopropyl, cyclobutyl, cyclopentyl, cyclohexyl, cycloheptyl and cyclooctyl.

Aryl includes phenyl and naphthyl optionally substituted by one or more substituents selected from halo, $C_{1-6}$ alkyl and $C_{1-6}$ alkoxy.

Values for monocyclic heteroaryl include pyridyl, pyrimidyl, pyrazinyl, pyrryl, imidazolyl, thienyl, furanyl, oxazole or thiazole (all possible isomers). Bicyclic heteroaryl include benzofuranyl, benzothiophenyl, indolyl and indazolyl, quinolyl and isoquinolyl (all possible isomers).

Values for 3 to 8 membered heterocyclyl, include cyclic polymethylene interrupted by one or two of N, O or S, linked through C or N, for example N-linked piperidinyl or pyrrolidinyl.

Halo includes fluoro, chloro, bromo and iodo.

A suitable bioisostere for the amide or ester linkage containing Y in formula (I), is of formula (d):

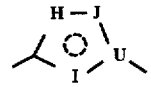

(d)

wherein
the dotted circle represents one or two double bonds in any position in the 5-membered ring; H, J and I independently represent oxygen, sulphur, nitrogen or carbon, provided that at least one of H, J and I is other than carbon; U represents nitrogen or carbon.

Suitable examples of (d) are as described for X, Y and Z in EP-A-328200 (Merck Sharp & Dohme Ltd.), such as an oxadiazole moiety.

A suitable value of Q is NR, such as NH.

Suitable examples of the $X_1$—$(CH_2)_x$—$X_2$ moiety include O—$(CH_2)_2$—O, O—$(CH_2)_3$—O, O—$CH_2$—O, O—$(CH_2)_2$—$NR_4$, O—$(CH_2)_2$—S or O—$CH_2$—$CONR_4$, wherein any of the methylene linkages are optionally mono- or di- substituted by $C_{1-6}$ alkyl groups, such as methyl. Preferably such $X_1$—$(CH_2)_2$—$X_2$ is O—$(CH_2)_2$—O.

Further suitable examples of the $X_1$—$(CH_2)_x$—$X_2$ include O—$(CH_2)_2$—$CH_2$, O—$(CH_2)_3$—$CH_2$, O—$CH_2$—$CH_2$, or corresponding values wherein $X_1$=$X_2$=$CH_2$, wherein any of the methylene linkages are optionally mono- or di-substituted by $C_{1-6}$ alkyl groups, such as methyl. Preferably such $X_1$—$(CH_2)_2$—$X_2$ is O—$(CH_2)_2$—$CH_2$.

$R_4$ and $R_5$ are often hydrogen. When $R_4$/$R_5$ is $C_{1-6}$ alkyl, it is often methyl. In particular $R_4$ and $R_5$ are methyl such that the disubstituent containing $X_1$ and $X_2$ is O—$C(CH_3)_2$—O.

$R_3$ is preferably hydrogen.

Y is preferably O or NH.

When Z is of sub-formula (a), $n^1$ is preferably 2, 3 or 4 when the azacycle is attached at the nitrogen atom and $n^1$ is preferably 1 when the azacycle is attached at a carbon atom, such as the 4-position when q is 2.

When Z is of sub-formula (b), $n^2$ is preferably such that the number of carbon atoms between the ester or amide linkage is from 2 to 4 carbon atoms.

Suitable values for p and m include p=m=1; p=0, m=1, p=1, m=2, p=2, m=1.

When Z is of sub-formula (c), $n^3$ is preferably 2, 3 or 4.

$R_8$ and $R_9$ are preferably both alkyl, especially one of $R_8$ and $R_9$ is $C_4$ or larger alkyl.

Specific values of Z of particular interest are as follows:

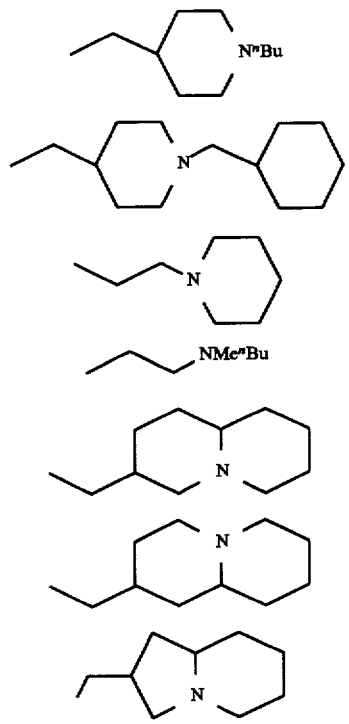

(i)
(ii)
(iii)
(iv)
(v)
(vi)
(vii)

The invention also provides novel compounds within formula (I) with side chains (i), (ii), (iii), (iv), (v), (vi) or (vii). In a further aspect, the piperidine ring in (i), (ii) or (iii) may be replaced by pyrrolidinyl or azetidinyl, and/or the N-substituent in (i) or (ii) may be replaced by $C_3$ or larger alkyl or optionally substituted benzyl.

In an alternative aspect, the N-substituent in formula (i) or (ii) may be replaced by $(CH_2)_n R^4$ as defined in formula (I) and in relation to the specific examples of EP-A-501322, or it may be replaced by a substituent The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

Examples of pharmaceutically acceptable salts include quaternary derivatives of the compounds of formula (I) such as the compounds quaternised by compounds $R_x$—T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

It will also be realised that the $(CH_2)_n 2$ moiety in compounds of formula (I) wherein Z is (b), may adopt an α or β or configuration with respect to the fused azabicyclic moiety.

The compounds of formula (I) may be prepared by conventional coupling of the $X_1$/$X_2$ moiety with Z. Suitable methods are as described in GB 2125398A (Sandoz Limited), GB 1593 146A and EP-A-36269 (Beecham Group p.l.c.), EP-A-429984 (Nisshin Flour Milling Co.) and EP-A-328200 (Merck Sharp & Dohme Limited). Reference is also made to EP-A-501322 (Glaxo Group Limited).

Aza(bi)cyclic side chain intermediates are known compounds or may be prepared according to the methods described in the aforementioned patent publications in the name of SmithKline Beecham p.l.c.

The compounds of the present invention are 5-$HT_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhoea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastro-oesophageal reflux disease and dyspepsia. Antiemetic activity is determined in known animal models of cytotoxic-agent/radiation induced emesis.

Specific cardiac 5-$HT_4$ receptor antagonists which prevent atrial fibrillation and other atrial arrhythmias associated with 5-HT, would also be expected to reduce occurrence of stroke (see A. J. Kaumann 1990, Naumyn-Schmiedeberg's Arch. Pharmacol. 342, 619–622, for appropriate animal test method).

Anxiolytic activity is likely to be effected via the hippocampus (Dumuis et al 1988, Mol Pharmacol., 34, 880–887).

Activity can be demonstrated in standard animal models, the social interaction test and the X-maze test.

Migraine sufferers often undergo situations of anxiety and emotional stress that precede the appearance of headache (Sachs, 1985, Migraine, Pan Books, London). It has also been observed that during and within 48 hours of a migraine attack, cyclic AMP levels are considerably increased in the cerebrospinal fluid (Welch et al., 1976, Headache 16, 160–167). It is believed that a migraine, including the prodomal phase and the associated increased levels of cyclic AMP are related to stimulation of 5-$HT_4$ receptors, and hence that administration of a 5-$HT_4$ antagonist is of potential benefit in relieving a migraine attack.

Other CNS disorders of interest include schizophrenia, Parkinson's disease and Huntingdon's chorea.

The invention also provides a pharmaceutical composition comprising a compound of formula (I), or a pharmaceutically acceptable salt thereof, and a pharmaceutically acceptable carrier.

Such compositions are prepared by admixture and are usually adapted for enteral such as oral, nasal or rectal, or parenteral administration, and as such may be in the form of tablets, capsules, oral liquid preparations, powders, granules, lozenges, reconstitutable powders, nasal sprays, suppositories, injectable and infusable solutions or suspensions. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of irritable bowel syndrome, dyspepsia, atrial arrhythmias and stroke, anxiety and/or migraine in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated within the aforementioned dosage ranges.

The invention also provides a compound of formula (I) or a pharmaceutically acceptable salt thereof for use as an active therapeutic substance, in particular for use in the treatment of irritable bowel syndrome, gastro-oesophageal reflux disease, dyspepsia, atrial arrhythmias and stroke, anxiety and/or migraine.

The following Examples illustrates the preparation of compounds of formula (I), and the following Descriptions relate to the preparation of intermediates.

DESCRIPTION 1

A stirred solution of 8-acetamido-1,4-benzodioxan-5-carboxylic acid (GB 1 571 278) (2.5 g, 0.0105 mole)in methanol (60 ml) was treated with concentrated sulphuric acid (2 ml) and the solution kept at room temperature for 20 hours, then concentrated in vacuo to approxiamately 10 ml volume. The residue was treated with water (30 ml), basified with potassium carbonate and a precipitate was produced. This was filtered off, washed with water and dried to afford methyl 8-amino-1,4-benzodioxan-5-carboxylate as a white solid (1.96 g, 89%). $^1$H NMR (CDCl$_3$) δ:7.38(d,1 H), 6.28(d,1 H), 4.25–4.43(m,4 H), 4.12(br s,2 H), 3.83(s,3 H).

b) Concentrated sulphuric acid (6.5 ml) was treated cautiously with stirring at 5°–10° C. with glacial acetic acid (12 ml) and to the resulting solution was added methyl 8-amino-1,4-benzodioxan-5-carboxylate (1.5 g, 0.0072 mole). The mixture was stirred at room temperature for 1 h, then treated portionwise over 45 minutes with potassium nitrate (0.85 g, 0.0084 mole). The mixture was stirred for a further 4 h then poured into water (100 ml) and basified with potassium carbonate. A precipitate was produced and this was filtered off, washed with water and dried to afford methyl 8-amino-7-nitro-1,4-benzodioxan-5-carboxylate as a yellow solid (0.30 g). The filtrate was extracted with ethyl acetate and the extract dried ($Na_2SO_4$) and concentrated in vacuo to afford a further 1.1 g of the product as an orange solid. $^1$H NMR ($CDCl_3$) δ:8.50(s,1 H), 6.0–7.0(v br,2 H), 4.30–4.55(m,4 H), 3.87(s,3 H).

c) A stirred suspension of methyl 8-amino-7-nitro-1,4-benzodioxan-5-carboxylate (300 mg, 0.0012 mole) in ethanol (30 ml) together with glacial acetic acid (5 ml) was hydrogenareal over 10% Pd-C (100 mg) at atmospheric pressure and temperature for 5 h. The catalyst was filtered off and the filtrate concentrated in vacuo. The residue was basified with concentrated potassium carbonate solution and extracted with ethyl acetate. The extract was dried ($Na_2SO_4$) and concentrated in vacuo to afford methyl 7,8-diamino-1,4-benzodioxan-5-carboxylate as a beige solid (240 mg, 92%). $^1$H NMR ($CDCl_3$) δ:6.91(s,1 H), 4.21(s,4 H), 3.96(br s,2 H), 3.74(s,3 H), 3.0(br s,2 H).

d) A solution of methyl 7,8-diamino-1,4-dioxan-5-carboxylate (240 mg, 1.07 mmole) in formic acid (15 ml) was heated under reflux for 3 h. The solution was concentrated in vacuo and the residue basified with potassium carbonate solution and a white solid was produced. This was filtered off, washed with water and dried to give methyl 1 H-7,8-dihydro-[1,4]-dioxino[2,3-g]benzimidazole-5-carboxylate (110 mg, 44%). $^1$H NMR ($d^6$DMSO) δ:8.19(s,1 H), 7.55(s,1 H), 4.30–4.45(m,4 H), 3.78(s,3 H), 3.6 (v br, 1 H).

DESCRIPTION 2

(1-Butyl-4-piperidinyl)methanol

A mixture of ethyl isonipecotate (102 g, 0.65 mole) and 1-bromobutane (72 ml, 0.67 mole) in ethanol (1.2 L) was treated with anhydrous potassium carbonate (180 g, 1.3 mole) and heated under reflux for 2 h. The mixture was allowed to cool and then filtered through kieselguhr. The filtrate was concentrated in vacuo to leave a yellow oil, which was dissolved in ether (300 ml) and added dropwise over 20 minutes to a stirred suspension of lithium aluminium hydride (50 g, 1.3 mole) in ether (500 ml) at 0° C. under nitrogen. The mixture was stirred at room temperature for 18 h, then cooled to 0° C. and treated with water (50 ml), 10% NaOH solution (50 ml) and water (150 ml). The mixture was filtered through keiselguhr and the filtrate concentrated under vacuum to leave a pale yellow oil, which was distilled to afford the title compound (D2) as a colourless oil (88.5 g, 80%) bp 102°–108° C. at 0.1 mm Hg. $^1$H NMR ($CDCl_3$) δ:3.48(d,2 H), 2.88–3.03(m,2 H), 2.25–2.38(m,2 H), 2.10(br s, 1 H), 1.66–2.00(m,4 H), 1.17–1.60(m,7 H), 0.90(t,3 H).

EXAMPLE 1

(1-Butyl-4-piperidinyl)methyl 1 H-7,8-dihydro-[1,4]-dioxino[2,3-g]benzimidazole-5-carboxylate [$R_1'R_2$=—NH—CH=N—, $R_3$=H, $R_4^1,R_4^2$=H, $X_1,X_2$=O, x=2, Y=O, Z=(i)]

A stirred solution of (1-butyl-4-piperidinyl)methanol (D2, 290 mg, 0.0017 mole) in THF (20 ml) under argon at 5° C. was treated with 1.5M methyllithium in ether (0.67 ml, 0.0010 mole). After 10 minutes the solution was treated with solid methyl 1 H-7,8-dihydro-[1,4]-dioxino[2,3-g]benzimidazole-5-carboxylate (D 1, 100 mg, 0.43 mmole) and heated under reflux for 3 h. The mixture was then treated dry with DMF (15 ml) to aid solubility, followed by more methyl 1 H-7,8-dihydro-[1,4]-dioxino[2,3-g]benzimidazole-5-carboxylate (200 mg, 0.86 mmole) and (1-butyl-4-piperidinyl)methanol (290 mg, 0.0017 mole) and heated under reflux for 6 h. The mixture was allowed to cool, then concentrated in vacuo and the residue treated with 10% $Na_2CO_3$ solution and extracted with chloroform. The extract was dried ($Na_2SO_4$) and concentrated in vacuo to afford a beige solid, which was washed with n-pentane to remove excess alcohol and then chromatographed on silica gel eluting with 0–10% methanol/chloroform. The title compound was obtained as a beige solid (60 mg), which was converted to its oxalate salt and crystallized from acetone as a beige solid mp 123°–127° C. $^1$H NMR ($CDCl_3$) δ:8.15(s,1 H), 7.70(s,1 H), 6.5–8.5(v br,1 H), 4.39(m,4 H), 4.18(d,2 H), 3.12(br d,2 H), 2.40–2.55(m,2 H), 2.00–2.20(m,2 H), 1.75–1.95(m,3 H), 1.46–1.72(m,4 H), 1.20–1.43(m,2 H), 0.91 (t,3 H).

The following compounds are prepared from the corresponding acid and lithium-(1-butyl-4-piperidinyl)methoxide via the imidazolide.

(1-Butyl-4-piperidinyl)methyl 1 H-7,8-dihydropyrano[1,4-g]dioxino[2,3-g]carboxylate [$R_1$—$R_2$=—NH—CH=CH—, $R_3$=H, $R_4^1,R_4^2$=H, $X_1,X_2$=O, x=2, Y=O, Z=(i)]

(1-Butyl-4-piperidinyl)methyl 1 H-3,7,8,9-tetrahydropyrano[3,2-e]indolecarboxylate [$R_1$—$R_2$=—C=CH—NH—, $R_3$=H, $R_4^1,R_4^2$=H, $X_1$=O, $X_2$=$CH_2$ x=2, Y=O, Z=(i)]

5-HT$_4$ RECEPTOR ANTAGONIST ACTIVITY

1) Guinea pig colon

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% $CO_2$ in $O_2$ and maintained at 37° C. In all experiments, the Krebs solution also contains methiothepin $10^{-7}$M and granisetron $10^{-6}$M to block effects at 5-HT$_1$, 5-HT$_2$ and 5-HT$_3$ receptors.

After construction of a simple concentration-response curve with 5-HT, using 30s contact times and a 15 min dosing cycle, a concentration of 5-HT is selected so as to obtain a contraction of the muscle approximately 40–70% maximum($10^{-9}$M approx). The tissue is then alternately dosed every 15 min with this concentration of 5-HT and then with an approximately equi-effective concentration of the nicotine receptor stimulant, dimethylphenylpiperazinium (DMPP). After obtaining consistent responses to both 5-HT and DMPP, increasing concentrations of a putative 5-HT$_4$ receptor antagonist are then added to the bathing solution. The effects of this compound are then determined as a percentage reduction of the contractions evoked by 5-HT or by DMPP. From this data, pIC$_{50}$ values are determined, being defined as the -log concentration of antagonist which reduces the contraction by 50%. A compound which reduces the response to 5-HT but not to DMPP is believed to act as a 5-HT$_4$ receptor antagonist.

The compound of Example 1 had a pIC$_{50}$ value of 6.78 (±0.11) (n=4)

We claim:

1. Compounds of formula (I), or pharmaceutically acceptable salts thereof:

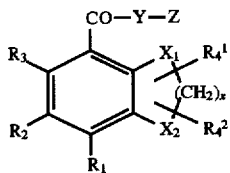

wherein $X_1$—$(CH_2)_x$—$X_2$ and the aromatic carbon atoms to which they are attached form a 5–7 membered ring $X_1$ is O or S; $X_2$ is O or S; or one of $X_1$ and $X_2$ is O, S or $CH_2$ and the other is $CH_2$;

x is 1 or 2;

$R_1$ and $R_2$ together are Q—$CH_2$—$CH_2$, Q—CH=CH, or Q—CH=N where Q is linked either to the $R_1$ or the $R_2$ substitution position and Q is O, S or $NR_r$ wherein $R_r$ is hydrogen or $C_{1-6}$ alkyl;

$R_3$ is hydrogen, halo, $C_{1-6}$ alkyl, $C_{1-6}$ alkoxy or amino;

$R_4^1$ and $R_4^2$ are independently hydrogen or $C_{1-6}$ alkyl;

Y is O or NH;

Z is of sub-formula (a):

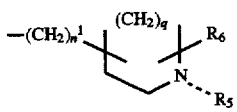

wherein $n^1$ is 1, 2, 3 or 4;

q is 0, 1, 2 or 3;

$R_5$ is hydrogen, $C_{1-12}$ alkyl, aralkyl or $R_5$ is $(CH_2)_z$—$R_{10}$ wherein z is 2 or 3 and $R_{10}$ is selected from cyano, hydroxyl, $C_{1-6}$ alkoxy, phenoxy, $C(O)C_{1-6}$ alkyl, $COC_6H_5$, —$CONR_{11}R_{12}$, $NR_{11}COR_{12}$, $SO_2NR_{11}R_{12}$ or $NR_{11}SO_2R_{12}$ wherein $R_{11}$ and $R_{12}$ are hydrogen or $C_{1-6}$ alkyl; or $R_5$ is straight or branched chain alkylene of chain length 1–6 carbon atoms terminally substituted by aryl, 3 to 8 membered cycloalkyl, 3 to 8 membered heterocyclyl, 5 or 6 membered monocyclic heteroaryl or 9 or 10 membered fused bicyclic heteroaryl linked through carbon, $C_{2-7}$ alkoxycarbonyl, or secondary or tertiary hydroxy substituted $C_{1-6}$ alkyl; and $R_6$ is hydrogen or $C_{1-6}$ alkyl;

or a compound of formula (I) wherein the CO—Y linkage is replaced by a heterocyclic bioisostere.

2. A compound according to claim 1 wherein $R_1$ and $R_2$ are joined to form —NH—CH=N—.

3. A compound according to claim 1 wherein the moiety attached to CO—Y—Z in formula (I) is wherein:

$R_1$—$R_2$ are together —NH—CH=N—, $R_3$ is H, $R_4^1$ and $R_4^2$ are H, $X_1$ and $X_2$ are O, and x is 2;

$R_1$—$R_2$ are together —NH—CH=CH—, $R_3$ is H, $R_4^1$ and $R_4^2$ are H, $X_1$ and $X_2$ are O, and x is 2; or $R_1$—$R_2$ are together —C=CH—NH—, $R_3$ is H, $R_4^1$ and $R_4^2$ are H, $X_1$ is O, $X_2$ is $CH_2$, and x is 2.

4. A compound according to claim 1 wherein Z is of sub-formula (a) and $(CH_2)_n 1$ is attached at a carbon atom of the azacycle.

5. A compound according to claim 4 wherein Z is N-substituted 4-piperidinylmethyl.

6. A compound according to claim 5 wherein the N-substituent is $C_2$ or greater alkyl, or optionally substituted benzyl.

7. A compound according to claim 1 wherein Y is NH.

8. (1-Butyl-4-piperidinyl)methyl 1 H-7,8-dihydro-[1,4]-dioxino[2,3-g]benzimidazole-5-carboxylate.

9. A pharmaceutical composition comprising a compound according to claim 1, and a pharmaceutically acceptable carrier.

10. A method of treating gastrointestinal disorders or cardiovascular disorders which comprises administering an effective amount of a compound according to claim 1.

11. A method of treating migraine, anxiety, schizophrenia, Parkinson's disease and Huntington's chorea which comprises the administering an effective amount of a compound according to claim 1.

12. A method of treating atrial arrhythmia or stroke which comprises administering an effective amount of a compound according to claim 1.

13. A method of treating urinary incontinence which comprises administering an effective amount of a compound according to claim 1.

14. A method of treating irritable bowel syndrome which comprises administering an effective amount of a compound according to claim 1.

* * * * *

UNITED STATES PATENT AND TRADEMARK OFFICE
CERTIFICATE OF CORRECTION

PATENT NO : 5,705,509
DATED : January 6, 1998
INVENTOR(S): Gaster, et al.

It is certified that error appears in the above-identified patent and that said Letters Patent is hereby corrected as shown below:

In column 10, line 33, claim 11, please delete the word "the" before the phrase "administering an effective amount".

Signed and Sealed this

Eighteenth Day of May, 1999

*Attest:*

Q. TODD DICKINSON

*Attesting Officer*      *Acting Commissioner of Patents and Trademarks*